(12) United States Patent
Cuthbertson et al.

(10) Patent No.: US 7,410,943 B2
(45) Date of Patent: Aug. 12, 2008

(54) IMAGING AGENTS

(75) Inventors: Alan Cuthbertson, Oslo (NO); Magne Solbakken, Oslo (NO)

(73) Assignee: GE Healthcare AS, Oslo (NO)

( * ) Notice: Subject to any disclaimer, the term of this patent is extended or adjusted under 35 U.S.C. 154(b) by 0 days.

(21) Appl. No.: 10/566,487

(22) PCT Filed: Jul. 21, 2004

(86) PCT No.: PCT/GB2004/003150

§ 371 (c)(1),
(2), (4) Date: Jan. 30, 2006

(87) PCT Pub. No.: WO2005/012335

PCT Pub. Date: Feb. 10, 2005

(65) Prior Publication Data

US 2006/0193773 A1  Aug. 31, 2006

(30) Foreign Application Priority Data

Jul. 30, 2003  (GB)  ................... 0317815.9

(51) Int. Cl.
*A61K 38/00* (2006.01)
*A61K 38/31* (2006.01)
*A61K 49/00* (2006.01)
(52) U.S. Cl. ............... 514/2; 530/311; 424/9.1
(58) Field of Classification Search ........ 514/2
See application file for complete search history.

(56) References Cited

U.S. PATENT DOCUMENTS 5,888,474 A    3/1999 Lister-James et al.

FOREIGN PATENT DOCUMENTS

| WO | WO/1995/014714 | * | 6/1995 |
| WO | 01/77145 | | 10/2001 |
| WO | 02/20610 | | 3/2002 |
| WO | 02/062819 | | 8/2002 |
| WO | 03/006491 | | 1/2003 |

OTHER PUBLICATIONS

Int'l Search Report dated Nov. 2004 for PCT/GB2004/003150.

Pearson, D.A. et al., "Thrombus Imaging Using Technetium-99M-Labeled High Potency GPIIB/IIIA Receptor Antagonists. Chemistry and Initial Biological Studies" Journal of Medicinal Chemistry, American Chemical society, Washington, US, vol. 39, No. 7, 1996 pp. 1372-1382.
Harris, T.D., et.al., "Tc-99m-labeled Fibrinogen Receptor Antagonists: Design and Synthesis of Cyclic RGD Peptides for the Detection of Thrombi" Bioorganic & Medicinal Chemistry Letters, Oxford, GB, vol. 6, No. 15, Aug. 1996 pp. 1741-1746.

* cited by examiner

*Primary Examiner*—Cecilia Tsang
*Assistant Examiner*—Maury Audet

(57) ABSTRACT

The invention relates to compounds of formula (I): and their use as targeting vectors that bind to receptors associated with angiogenesis. Such compounds may thus be used for diagnosis or therapy of, for example, malignant diseases, heart diseases, endometriosis, inflammation-related diseases, rheumatoid arthritis and Kaposi's sarcoma.

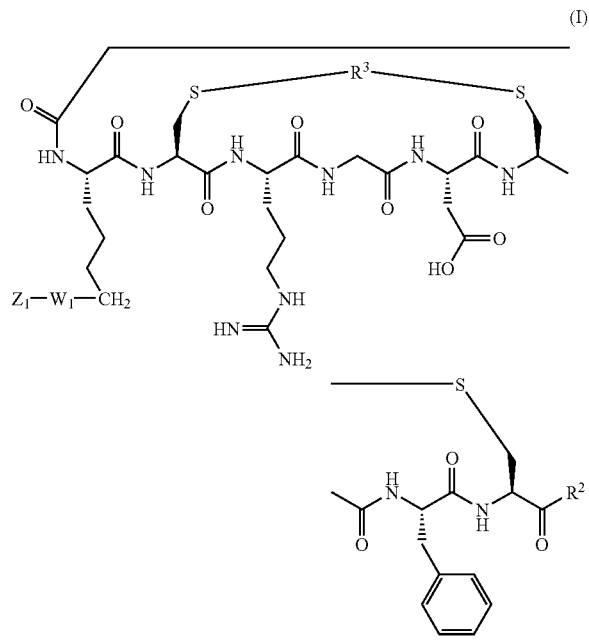

13 Claims, No Drawings

IMAGING AGENTS

This application is a filing under 35 U.S.C. 371 of international application number PCT/GB2004/003150, filed Jul. 21, 2004, which claims priority to application number 0317815.9 filed Jul. 30, 2003, in Great Britain the entire disclosure of which is hereby incorporated by reference.

The present invention relates to new peptide-based compounds and their use for diagnostic imaging techniques such as single-photon emission tomography (SPECT) or positron emission tomography (PET). More specifically the invention relates to the use of such peptide-based compounds as targeting vectors that bind to receptors associated with angiogenesis, in particular integrin receptors, for example, the αvβ3 integrin receptor. Such compounds may thus be used for diagnosis or therapy of, for example, malignant diseases, heart diseases, endometriosis, inflammation-related diseases, rheumatoid arthritis and Kaposi's sarcoma.

New blood vessels can be formed by two different mechanisms: vasculogenesis or angiogenesis. Angiogenesis is the formation of new blood vessels by branching from existing vessels. The primary stimulus for this process may be inadequate supply of nutrients and oxygen (hypoxia) to cells in a tissue. The cells may respond by secreting angiogenic factors, of which there are many; one example, which is frequently referred to, is vascular endothelial growth factor (VEGF). These factors initiate the secretion of proteolytic enzymes that break down the proteins of the basement membrane, as well as inhibitors that limit the action of these potentially harmful enzymes. The other prominent effect of angiogenic factors is to cause endothelial cells to migrate and divide. Endothelial cells that are attached to the basement membrane, which forms a continuous sheet around blood vessels on the contralumenal side, do not undergo mitosis. The combined effect of loss of attachment and signals from the receptors for angiogenic factors is to cause the endothelial cells to move, multiply, and rearrange themselves, and finally to synthesise a basement membrane around the new vessels.

Angiogenesis is prominent in the growth and remodelling of tissues, including wound healing and inflammatory processes. Tumours must initiate angiogenesis when they reach millimetre size in order to keep up their rate of growth.

Angiogenesis is accompanied by characteristic changes in endothelial cells and their environment. The surface of these cells is remodelled in preparation for migration, and cryptic structures are exposed where the basement membrane is degraded, in addition to the variety of proteins which are involved in effecting and controlling proteolysis. In the case of tumours, the resulting network of blood vessels is usually disorganised, with the formation of sharp kinks and also arteriovenous shunts. Inhibition of angiogenesis is also considered to be a promising strategy for antitumour therapy. The transformations accompanying angiogenesis are also very promising for diagnosis, one example being malignant disease, but the concept also shows great promise in inflammation and a variety of inflammation-related diseases, including atherosclerosis, the macrophages of early atherosclerotic lesions being potential sources of angiogenic factors.

Many ligands involved in cell adhesion contain the tripeptide sequence arginine-glycine-aspartic acid (RGD). The RGD sequence appears to act as a primary recognition site between the ligands presenting this sequence and receptors on the surface of cells. It is generally believed that secondary interactions between the ligand and receptor enhance the specificity of the interaction. These secondary interactions might take place between moieties of the ligand and receptor that are immediately adjacent to the RGD sequence or at sites that are distant from the RGD sequence.

The efficient targeting and imaging of integrin receptors associated with angiogenesis in vivo demands therefore a selective, high affinity RGD based vector that is chemically robust and stable. Furthermore, the route of excretion is an important factor when designing imaging agents in order to reduce problems with background.

WO 03/006491 describes peptide-based compounds which target integrin receptors associated with angiogenesis. However, there exists a need for further such peptide-based compounds having utility for diagnostic imaging techniques such as SPECT and PET as well as for therapeutic treatment. In particular, there is a need for peptide-based compounds having greater stability to the reaction conditions used to introduce a reporter moiety such as a radionuclide.

Therefore, according to a first aspect of the invention, there is provided a compound of formula (I):

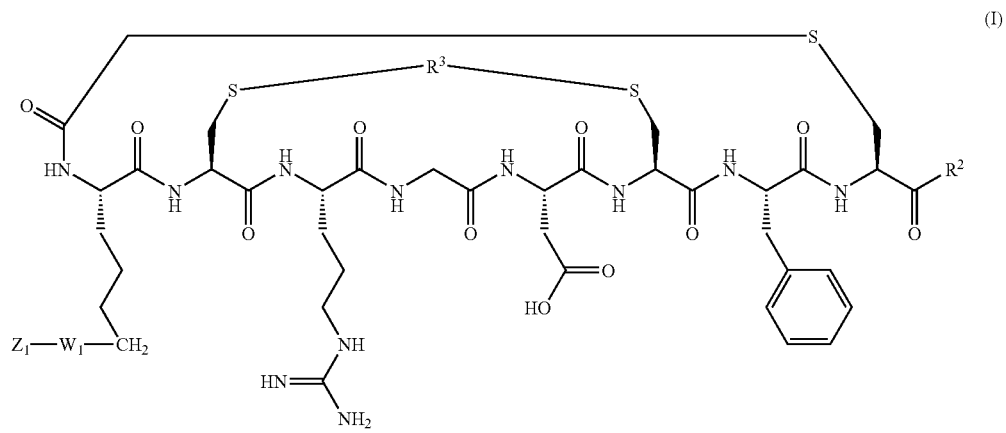

wherein
R² is

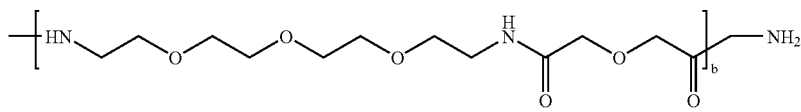

wherein b is an integer of from 0 to 10;
R³ is a $C_{1-4}$ alkylene or $C_{2-4}$ alkenylene bridge;
$W_1$ is absent or represents a spacer moiety which is a $C_{1-30}$ hydrocarbyl group optionally including 1 to 10 heteroatoms selected from oxygen, nitrogen, and sulphur, and is preferentially derived from glutaric and/or succinic acid and/or a polyethyleneglycol based unit and/or a unit of Formula:

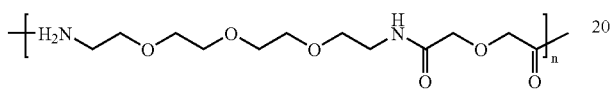

$Z_1$ is an antineoplastic agent, a chelating agent or a reporter moiety.

Suitable chelating agents, $Z_1$ include those of Formula A

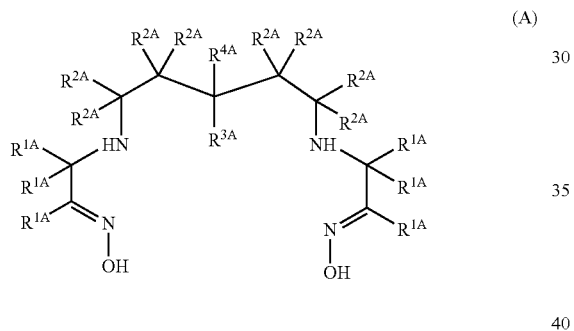

(A)

where:
each $R^{1A}$, $R^{2A}$, $R^{3A}$ and $R^{4A}$ is independently an $R^A$ group;
each $R^A$ group is independently H or $C_{1-10}$ alkyl, $C_{3-10}$ alkylaryl, $C_{2-10}$ alkoxyalkyl, $C_{1-10}$ hydroxyalkyl, $C_{1-10}$ alkylamine, $C_{1-10}$ fluoroalkyl, or 2 or more $R^A$ groups, together with the atoms to which they are attached form a carbocyclic, heterocyclic, saturated or unsaturated ring,
or $Z_1$ can represent a chelating agent given by formula (i), (ii), (iii), or (iv)

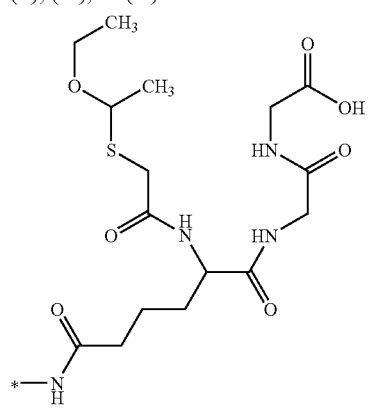

(i)

-continued

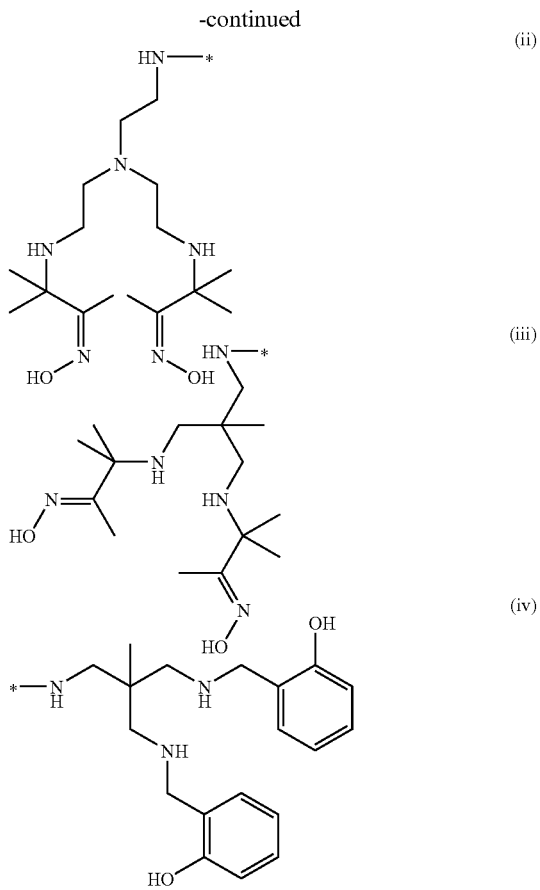

A preferred example of a chelating agent is represented by formula (v).

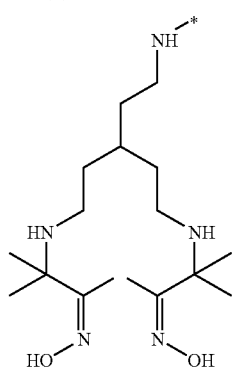

(V)

Compounds of formula (I) comprising chelating agents of Formula A can be radiolabelled to give good radiochemical purity (RCP), at room temperature, under aqueous conditions at near neutral pH.

The role of the spacer moiety $W_1$ is to distance $Z_1$ from the active site of the peptide component. For example, the spacer moiety $W_1$ may distance a bulky antineoplastic agent or chelating agent from the active site of the peptide.

Further examples of suitable chelating agents $Z_1$ are disclosed in U.S. Pat. No. 4,647,447, WO89/00557, U.S. Pat. No. 5,367,080, U.S. Pat. No. 5,364,613 and further include those defined in Table I.

TABLE I

| Class of ligand | Structure | Definitions |
| --- | --- | --- |
| Amineoxime | 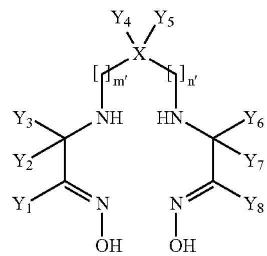 | Y1-8 can be H, alkyl, aryl or combinations thereof and Y4 or Y5 contains a suitable functionality such that it can be conjugated to the peptide vector - e.g. preferably alkylamine, alkylsulphide, alkoxy, alkyl carboxylate, arylamine, aryl sulphide or α-haloacetyl<br>X = C or N when m' = n' = 1<br>X = N when m' = n' = 2 |
| MAG3 type | 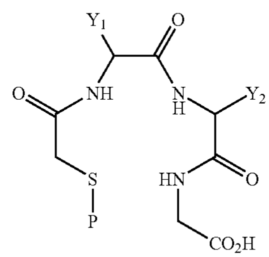 | P = protecting group (preferably. benzoyl, acetyl, EOE); Y1, Y2 contains a suitable functionality such that it can be conjugated to the peptide vector; preferably H (MAG3), or the side chain of any amino acid, in either L or D form. |
| G4 type ligands | 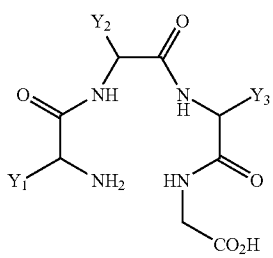 | Y1, Y2, Y3 - contains a suitable functionality such that it can be conjugated to the peptide vector; preferably H, or the side chain of any amino acid, in either L or D form. |
| Tetra-amine ligands | 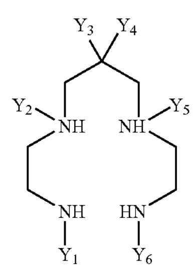 | Y1-Y6 can be H, alkyl, aryl or combinations thereof where the Y1-6 groups contain one or more functional moieties such that the chelate can be conjugated to the vector - e.g. preferably alkylamine, alkylsulphide, alkoxy, alkyl carboxylate, arylamine, aryl sulphide or α-haloacetyl |
| Cylam type ligands | 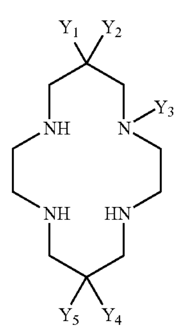 | Y1-5 can be H, alkyl, aryl or combinations thereof and where Y1-5 groups contain one or more functional moieties such that the chelate can be conjugated to the vector - e.g. preferably alkylamine, alkylsulphide, alkoxy, alkyl carboxylate, arylamine, aryl sulphide or α-haloacetyl |

TABLE I-continued

| Class of ligand | Structure | Definitions |
| --- | --- | --- |
| Diaminediphenol | 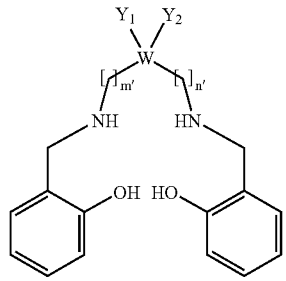 | Y1, Y2 - H, alkyl, aryl and where Y1 or Y2 groups contains a functional moiety such that the chelate can be conjugated to the vector - e.g. preferably alkylamine, alkylsulphide, alkoxy, alkyl carboxylate, arylamine, aryl sulphide or α-haloacetyl<br>W = C, N<br>m' = n' = 1 or 2 |
| HYNIC | 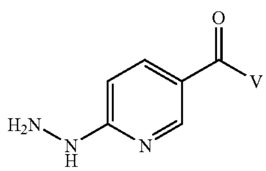 | V = linker to vector or vector itself. |
| Amide thiols | 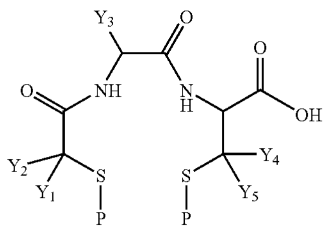 | P = protecting group (preferably. benzoyl, acetyl, EOE); Y1-5 = H, alkyl, aryl; or Y3 is a L or D amino acid side-chain or glycine and the carboxylate may be used for conjugation to the vector via an amide bond. Alternatively the $R_{1-5}$ groups may contain additional functionality such that the chelate can be conjugated to the vector - e.g. alkylamine, alkylsulphide, alkoxy, alkyl carboxylate, arylamine, aryl sulphide or α-haloacetyl. |

In one aspect of the present invention, $Z_1$ is represented by an antineoplastic agent. In this aspect the compound of formula (I) will target an angiogenic site associated with cancer and bring the antineoplastic agent to the diseased area. The antineoplastic agent may be represented by cyclophosphamide, chloroambucil, busulphan, methotrexate, cytarabine, fluorouracil, vinblastine, paclitaxel, doxorubicin, daunorubicin, etoposide, teniposide, cisplatin, amsacrine, docetaxel, but a wide range of other antineoplastic agents may also be used.

The reporter moieties ($Z_1$) in the compounds of formula (I) may be any moiety capable of detection either directly or indirectly in an in vivo diagnostic imaging procedure. Preferred are reporter moieties which emit or may be caused to emit detectable radiation (for example, a radionuclide such as a positron emitting radionuclide).

For magnetic resonancece (MR) imaging the reporter moiety will either be a non zero nuclear spin isotope (such as $^{19}F$) or a material having unpaired electron spins and hence paramagnetic, superparamagnetic, ferrimagnetic or ferromagnetic properties; for light imaging the reporter moiety will be a light scatterer (e.g. a coloured or uncoloured particle), a light absorber or a light emitter; for magnetometric imaging the reporter will have detectable magnetic properties; for electrical impedance imaging the reporter moiety will affect electrical impedance; and for scintigraphy, SPECT, PET, and the like, the reporter moiety will be a radionuclide.

Stated generally, the reporter moiety may be (1) a chelating agent as defined above, chelated to a metal or polyatomic metal-containing ion (i.e. TcO, etc), where the metal is a high atomic number metal (e.g. atomic number greater than 37), a paramagnetic species (e.g. a transition metal or lanthanide), or a radioactive isotope, (2) a covalently bound non-metal species which is an unpaired electron site (e.g. an oxygen or carbon in a persistent free radical), a high atomic number non-metal, or a radioisotope, (3) a polyatomic cluster or crystal containing high atomic number atoms, displaying cooperative magnetic behaviour (e.g. superparamagnetism, ferrimagnetism or ferromagnetism) or containing radionuclides.

Chelated metal reporter moieties are preferably selected from the group: $^{90}Y$, $^{99m}Tc$, $^{111}In$, $^{47}Sc$, $^{67}Ga$, $^{68}Ga$, $^{51}Cr$, $^{177m}Sn$, $^{62}Cu$, $^{167}Tm$, $^{97}Ru$, $^{188}Re$, $^{177}Lu$, $^{199}Au$, $^{203}Pb$ and $^{141}Ce$ and are chelated to a chelating group as defined above.

Methods for metallating any chelating agents present are within the level of skill in the art. Metals can be incorporated into a chelating agent by any one of three general methods: direct incorporation, template synthesis and/or transmetallation. Direct incorporation is preferred.

Thus it is desirable that the metal ion be easily complexed to the chelating agent, for example, by merely exposing or mixing an aqueous solution of the chelating agent-containing moiety with a metal salt in an aqueous solution preferably having a pH in the range of about 4 to about 11.The salt can be any salt, but preferably the salt is a water soluble salt of the metal such as a halogen salt, and more preferably such salts are selected so as not to interfere with the binding of the metal ion with the chelating agent. The chelating agent-containing moiety is preferably in aqueous solution at a pH of between about 5 and about 9, more preferably between pH about 6 to about 8.The chelating agent-containing moiety can be mixed with buffer salts such as citrate, carbonate, acetate, phosphate and borate to produce the optimum pH. Preferably, the buffer salts are selected so as not to interfere with the subsequent binding of the metal ion to the chelating agent.

The following isotopes or isotope pairs can be used for both imaging and therapy without having to change the radiolabelling methodology or chelating agent: $^{47}Sc_{21}$; $^{141}Ce_{58}$; $^{188}Re_{75}$; $^{177}Lu_{71}$; $^{199}Au_{79}$; $^{47}Sc_{21}$; $^{135}I_{53}$; $^{67}Cu_{29}$; $^{131}I_{53}$ and $^{123}I_{53}$; $^{188}Re_{75}$ and $^{99m}Tc_{43}$; $^{90}Y_{39}$ and $^{87}Y_{39}$; $^{47}Sc_{21}$ and $^{44}Sc_{21}$; $^{90}Y_{39}$ and $^{123}I_{53}$; $^{146}Sm_{62}$ and $^{153}Sm_{62}$; and $^{90}Y_{39}$ and $^{111}In_{49}$.

Preferred non-metal atomic reporters include radioisotopes such as $^{123}I$, $^{131}I$ and $^{18}F$ as well as non zero nuclear spin atoms such as $^{19}F$, and heavy atoms such as I.

In a preferred aspect of the invention, $Z_1$ in the compound of formula (I) comprises a positron emitting radionuclide incorporated either as a prosthetic group or by substitution or addition reactions, or by chelation. Suitable positron emitting radionuclides for this purpose include $^{11}C$, $^{18}F$, $^{15}O$, $^{13}N$, $^{75}Br$, $^{122}I$, $^{124}I$, $^{82}Rb$, $^{68}Ga$, and $^{62}Cu$, of which $^{11}C$ and $^{18}F$ are preferred. The resulting compound of formula (I) may thus be used in Positron Emission Tomography (PET) Imaging.

Therefore, according to a preferred aspect of the invention, there is provided a compound of formula (Ia):

wherein b is an integer of from 0 to 10;

$R^3$ is a $C_{1-4}$ alkylene or $C_{2-4}$ alkenylene bridge;

the Linker is a $C_{1-30}$ hydrocarbyl group optionally including 1 to 10 heteroatoms.

In the compounds of formula (Ia):
$R^3$ is preferably $C_{1-4}$ alkylene, and more preferably —$CH_2$—;
a is preferably an integer of from 1 to 10, and is most preferably 5;
b is preferably 1.

In formula (Ia) the Linker is a $C_{1-30}$ hydrocarbyl group optionally including 1 to 10 heteroatoms such as oxygen or nitrogen, and may be chosen to provide good in vivo pharmacokinetics, such as favourable excretion characteristics. Suitable Linker groups include alkyl, alkenyl, alkynyl chains,

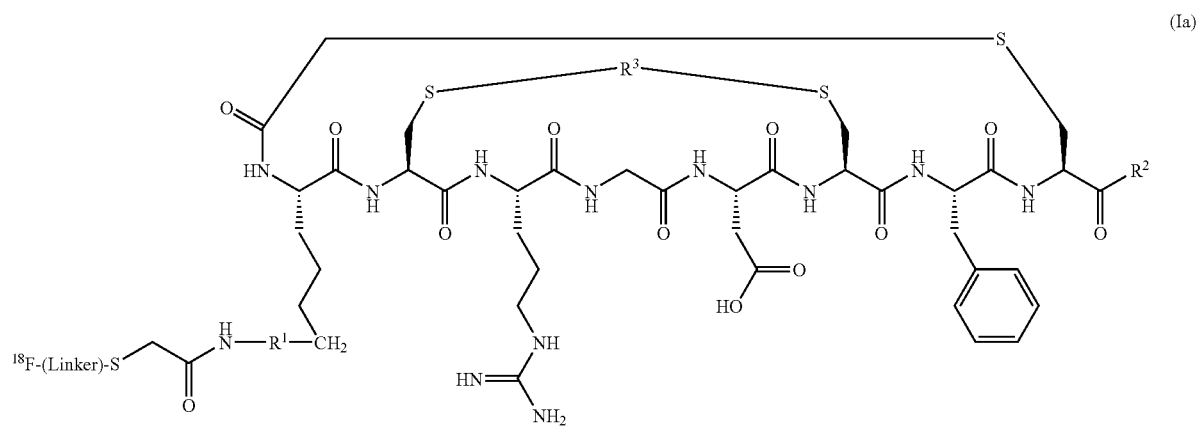

(Ia)

wherein
$R^1$ is either a bond or is

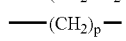

wherein a is an integer of from 1 to 30;
$R^2$ is aromatic, polyaromatic, and heteroaromatic rings, and polymers comprising ethyleneglycol, amino acid, or carbohydrate subunits. The Linker is preferably selected from (II), (III) and (IV):

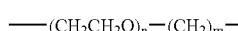 (II)

(III)

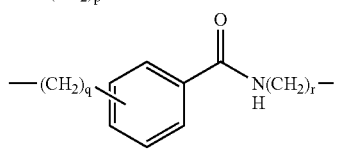 (IV)

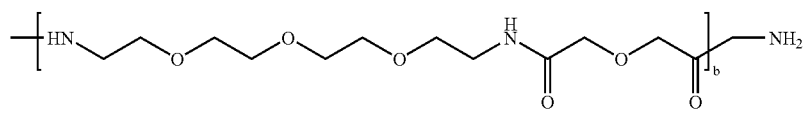

wherein:

n is an integer of 1 to 20;
m is an integer of 1 to 10;
p is an integer of 1 to 20;
q is an integer of 0 to 4;
r is an integer of 1 to 10.

In formula (II), n is typically 2 to 6, suitably 3, and m is typically 1 to 4, suitably 2.

In formula (III), p is typically 1 to 6, suitably 3.

In formula (IV), the group —$(CH_2)_q$— is suitably attached in the para position relative to the amide group, q is typically 0 to 4, suitably 1, and r is typically 1 to 4, suitably 2.

As shown in the in vitro competition binding assay below, the compounds of formula (I) and (Ia) bind to receptors associated with angiogenesis. These compounds may thus be useful for treatment, in vivo diagnosis and imaging of diseases and conditions associated with angiogenesis.

The term "diseases and conditions associated with angiogenesis" includes those diseases and conditions referred to below. Reference is also made in this regard to WO 98/47541.

Diseases and conditions associated with angiogenesis include different forms of cancer and metastasis, for example, breast, skin, colorectal, pancreatic, prostate, lung or ovarian cancer.

Other diseases and conditions associated with angiogenesis are inflammation (for example, chronic inflammation), atherosclerosis, rheumatoid arthritis and gingivitis.

Further diseases and conditions associated with angiogenesis are arteriovenous alformations, astrocytomas, choriocarcinomas, glioblastomas, gliomas, hemangiomas (childhood, capillary), hepatomas, hyperplastic endometrium, ischemic myocardium, endometriosis, Kaposi sarcoma, macular degeneration, melanoma, neuroblastomas, occluding peripheral artery disease, osteoarthritis, psoriasis, retinopathy (diabetic, proliferative), scleroderma, seminomas and ulcerative colitis.

Therefore, according to a further aspect of the invention, there is provided a compound of formula (I) or (Ia) for use in medicine, particularly in the in vivo diagnosis or imaging, for example by PET, of a disease or condition associated with angiogenesis.

In the alternative, there is provided a method for in vivo diagnosis or imaging of a disease or condition associated with angiogenesis which comprises the step of administering a compound of formula (I) or (Ia) to a human or animal body, followed by generation of an image, suitably a PET image, of part or all of said body. Further, there is provided a method for treatment of a disease or condition associated with angiogenesis which comprises the step of administering a therapeutically effective amount of a compound of formula (I) to a human or animal body.

The compounds of formula (I) or (Ia) are preferably administered in a radiopharmaceutical formulation. A "radiopharmaceutical formulation" is defined in the present invention as a formulation comprising a compound of formula (I) or (Ia) in a form suitable for administration to a mammal, such as a human. Administration is preferably carried out by injection of the radiopharmaceutical formulation as an aqueous solution. Such a radiopharmaceutical formulation may optionally contain further ingredients such as buffers, pharmaceutically acceptable solubilisers (for example cyclodextrins or surfactants such as Pluronic, Tween, or phospholipids), pharmaceutically acceptable stabilisers or antioxidants (such as ascorbic acid, gentisic acid or para-aminobenzoic acid) or bulking agents for lyophilisation (such as sodium chloride or mannitol). The radiopharmaceutical formulation is administered in an amount which gives a reliable image, taking into account the nature of the disease or condition being investigated, size of patient, and such other factors as would be apparent to a person skilled in the art. Where the reporter moiety comprises a metal, generally doses of from 0.001 to 5.0 mmoles of chelated imaging metal ion per kilogram of patient bodyweight are effective to achieve a reliable image. For PET, a suitable amount of the compound of formula (I) or (Ia) is 0.1 to 100 mCi, preferably 1 to 20 mCi.

Therefore, in a further aspect of the invention, there is provided a radiopharmaceutical formulation comprising a compound of formula (I) or (Ia) and one or more pharmaceutically acceptable excipients. The invention further provides a pharmaceutical formulation comprising a therapeutically effective amount of a compound of formula (I) or a salt thereof, together with one or more pharmaceutically acceptable adjuvants, excipients, or diluents.

An effective therapeutic dose of a compound of formula (I) will depend upon the condition and patient being treated, but in general will be in the range 1 pmol/kg to 1 mmol/kg bodyweight.

Compounds of formula (I) may be prepared using methods of organic synthesis including solid-phase methodology of Merrifield employing an automated peptide synthesiser (J. Am. Chem. Soc., 85: 2149 (1964)) and methods analogous to those described in WO 03/006491.The compounds of formula (I) may be purified using high performance liquid chromatography (HPLC).

A compound of formula (Ia) may be prepared from the corresponding compound of formula (V):

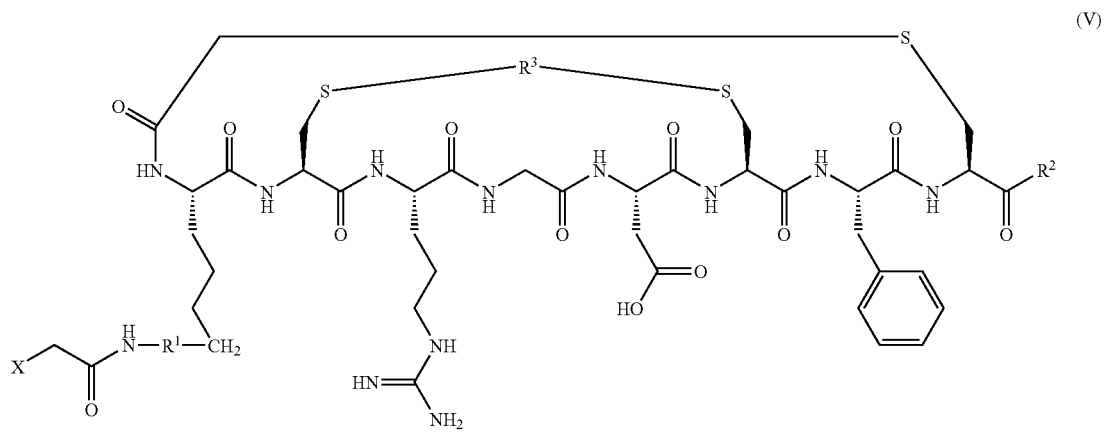

(V)

wherein $R^1$, $R^2$, and $R^3$ are as defined for the compound of formula (I) and X is a leaving group selected from chloro, bromo, and iodo, and is preferably chloro; by reaction with the appropriate compound of formula (VI):

$^{18}$F-(Linker)-SH    (VI)

wherein the Linker is as defined for the compound of formula (I).

Compounds of formula (V) are novel and thus represent a further aspect of the present invention.

The reaction of compounds of formulae (V) and (VI) may be performed using the methodologies described in international patent application WO 03/080544. In general terms, the reaction may be effected in a suitable solvent, for example in an aqueous buffer in the pH range 5 to 11, and at a non-extreme temperature of from 5 to 70° C., preferably at ambient temperature.

Compounds of formula (V) may be prepared by standard methods of peptide synthesis, for example, solid-phase peptide synthesis, for example, as described in Atherton, E. and Sheppard, R. C.; "Solid Phase Synthesis"; IRL Press: Oxford, 1989. WO 03/006491 also describes synthesis of analogous peptides and in this regard, is incorporated herein by reference. Incorporation of the bridging group $R^3$ may be effected by reaction of the corresponding peptide containing two free thiol 1 5 groups, with the relevant dichloroalkane or dichloroalkene (such as dichloromethane when $R^3$ is to be methylene). Incorporation of the group "X—CH$_2$C(O) —" in a compound of formula (V) may be achieved by reaction of the N-terminus or an amine-containing amino acid, preferably lysine, of the peptide with the reagent of formula (VI):

X—CH$_2$C(O)Z    (VII)

under standard conditions for peptide bond formation; wherein X is as defined for the compound of formula (V), and Z is —OH or a suitable activating group such as, chloro, bromo, fluoro, —OC(O)CH$_2$—X wherein X is as defined for the compound of formula (V), or when Z is —OH the acid may be activated using in situ agents such as 2-(1H-benzotriazole-1-yl)-1,1,3,3-tetramethyluronium hexafluorophosphate (HBTU) or N-[(dimethylamino)-1H-1,2,3-triazolo[4,5-b]pyridin-1-ylmethylene]-N-methylmethanaminium hexafluorophosphate N-oxide (HATU).

Compounds of formula (VI) may be prepared by standard methods such as those described in international patent application WO 03/080544, for example, from the corresponding compound of formula (VIa):

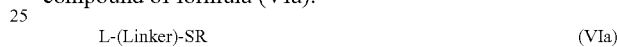

L-(Linker)-SR    (VIa)

wherein L is a leaving group such as p-toluenesulphonate, trifluoromethanesulphonate, or methanesulphonate, and the Linker is as defined for the compound of formula (VI) and R is hydrogen or a thiol protecting group; by reaction with cyclotron produced aqueous [$^{18}$F]-fluoride, suitably pre-activated by evaporation from a base (for example, from tetrabutylammonium or K$_2$CO$_3$/Kryptofix-222), in a suitable solvent such as acetonitrile, N,N-dimethylformamide, or dimethyl sulphoxide, typically at elevated temperature, for example 60 to 120° C., followed by removal of any thiol protecting group using standard methods.

Compounds of formula (VI) in which the Linker is of formula (II) may be prepared from the corresponding compound of formula (VIb):

L-(CH$_2$CH$_2$O)$_n$—(CH$_2$)$_m$—SR    (VIb)

wherein L is a leaving group such as p-toluenesulphonate, trifluoromethanesulphonate, or methanesulphonate, and n and m are as defined for the formula (II) and R is hydrogen or a thiol protecting group;

by reaction with cyclotron produced aqueous [$^{18}$F]-fluoride, suitably pre-activated by evaporation from a base (for example, from tetrabutylammonium or K$_2$CO$_3$/Kryptofix-222), in a suitable solvent such as acetonitrile, N,N-dimethylformamide, or dimethyl sulphoxide, typically at elevated temperature, for example 60 to 120° C., followed by removal of any thiol protecting group using standard methods.

Compounds of formula (VI) in which the Linker is of formula (III) may be prepared from the corresponding compound of formula (VIc):

L-(CH$_2$)$_p$—SR    (VIc)

wherein L is a leaving group such as p-toluenesulphonate, trifluoromethanesulphonate, or methanesulphonate, and p is as defined for the formula (III) and R is hydrogen or a thiol protecting group;

by reaction with cyclotron produced aqueous [$^{18}$F]-fluoride, suitably pre-activated by evaporation from a base (for example, from tetrabutylammonium or $K_2CO_3$/Kryptofix-222), in a suitable solvent such as acetonitrile, N,N-dimethylformamide, or dimethyl sulphoxide, typically at elevated temperature, for example 60 to 120° C., followed by removal of any thiol protecting group using standard methods.

Compounds of formula (VI) in which the Linker is of formula (IV) may be prepared from the corresponding compound of formula (VId):

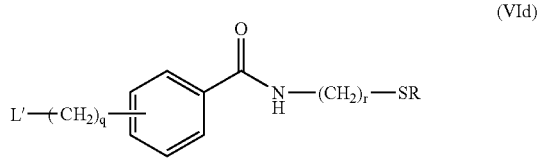

(VId)

wherein L' is a leaving group such as iodo, p-toluenesulphonate, trifluoromethanesulphonate, or methanesulphonate and when q is 0, L' can be nitro or an iodonium or ammonium salt, and q and rare as defined for the formula (IV) and R is hydrogen or a thiol protecting group;

by reaction with cyclotron produced aqueous $[^{18}F]$-fluoride, suitably pre-activated by evaporation from a base (for example, from tetrabutylammonium or $K_2CO_3$/Kryptofix-222), in a suitable solvent such as acetonitrile, N,N-dimethylformamide, or dimethyl sulphoxide, typically at elevated temperature, for example 60 to 120° C., followed by removal of any thiol protecting group using standard methods.

In formulae (VIa), (VIb), (VIc), and (VId), suitable thiol protecting groups include $(Phenyl)_3C$-(trityl) and others as may be found described in Protecting Groups in Organic Synthesis, Theodora W. Greene and Peter G. M. Wuts, published by John Wiley & Sons Inc. Removal of such thiol protecting groups may be effected by standard methods, such as those described in Greene. For example, where R is trityl, the free thiol may be formed by treatment with dilute acid, for example trifluoroacetic acid in a chlorinated solvent, such as dichloromethane.

In one preferred aspect, the compounds of formulae (VIa), (VIb), (VIc), and (VId) may be bound to a solid support, such as polymer beads or coatings, for example, a trityl or chlorotrityl resin. In this aspect, the excess reagents and by-products of the radio-fluorination reaction may be separated from the polymer-bound product by washing. Using the deprotection methods as described above, effects cleavage of the compound of formula (VI) from the solid support. This approach may be particularly suitable for automated production of the compounds of formula (VI). Alternatively, the by-products of thiol deprotection, where insoluble in the reaction mixture, may be removed by filtration.

According to a further aspect of the invention there is provided a kit for the preparation of a radiofluorinated peptide of formula (I) comprising a prosthetic group of formula (VIa), (VIb), (VIc), or (VId) and an activated peptide of formula (V).

In use of the kit, the compound of formula (VIa), (VIb), (VIc), or (VId) would be converted to the corresponding compound of formula (VI) using methods described above. Preferably, the compound of formula (VI) or a thiol protected precursor of any thereof, may be separated from waste reactants by passing the reaction mixture through a Solid Phase Extraction (SPE) cartridge. The SPE cartridge may comprise a graphite pad or $C_{18}$ stationary phase. Any thiol protecting group may be removed, for example, by addition of an acid such as trifluoroacetic acid. Where the thiol group in the compound of formula (VI) is protected with a hydrophobic group, such as a trityl group, the deprotection may conveniently be effected on the SPE cartridge, whereby the hydrophobic thiol protecting group (such as trityl) remains bound on the stationary phase while the labelled prosthetic group of formula (VI) is eluted in high purity and yield. The compound of formula (VI) would then be added to the compound of formula (V) or which may suitably be dissolved in aqueous buffer (pH 7-11). After reaction at a non-extreme temperature for 1 to 60 minutes, the labelled peptide may be purified, for example, by SPE and collected.

The invention is illustrated by way of the following Examples, in which these abbreviations are used throughout:
DCM: dichloromethane
TFA: trifluoroacetic acid
THF: tetrahydrofuran
HBTU: 2-(1H-benzotriazole-1-yl)-1,1,3,3-tetramethyluronium hexafluorophosphate
Boc: tert-butoxy-carbonyl
Fmoc: 9-fluorenylmethoxycarbonyl
TIS: triisopropylsilane

EXAMPLES

Example 1

Preparation of a 3-fluoro-propylsulfanyl Labelled RGD Containing Peptide

Title Compound:

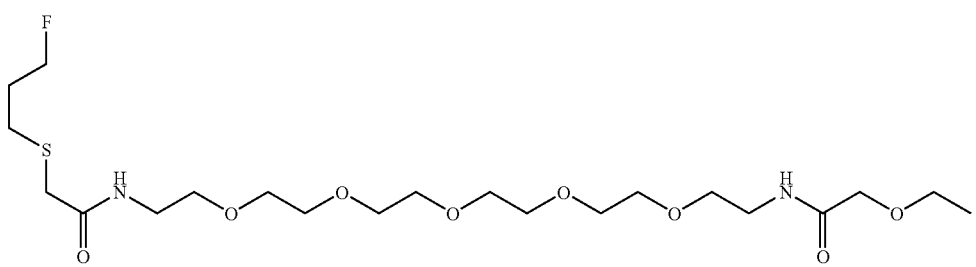

-continued

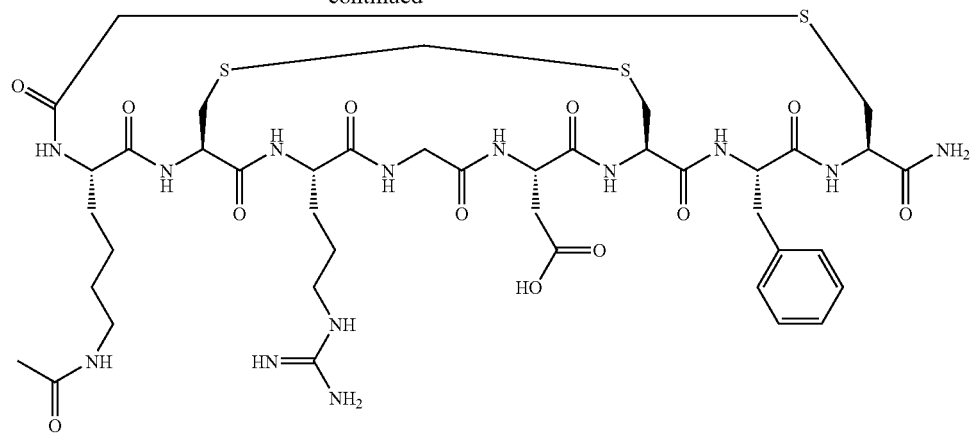

1a) Synthesis of 3-tritylsulfanyl-propan-1-ol

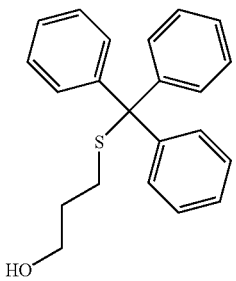

Trityl chloride (27.9 mg, 0.1 mmol) and triethyl amine (49 µl, 0.5 mmol) were dissolved in DCM (2 ml) before 3-mercapto-1-propanol (9 µl, 0.1 mmol) was added. DCM was evaporated under reduced pressure after 6 hours and the crude product purified by reverse phase preparative chromatography (Vydac 218TP1022 column; solvents A=water/0.1% TFA and B=CH$_3$CN/0.1% TFA; gradient 30-70% B over 40 min; flow 10 ml/minute; detection at 254 nm). A yield of 6 mg of purified material was obtained (analytical HPLC: column phenomenex Luna C18, 00B-4251-E0: solvents: A=water/ 0.1% TFA and B=CH$_3$CN/0.1% TFA; gradient 30-70% B over 10 min; flow 1.0 ml/minute; retention time 7.73 minutes detected at 214 and 254 nm). Structure verified by NMR.

1b) Synthesis of methanesulfonic acid 3-tritylsulfanyl-propyl ester

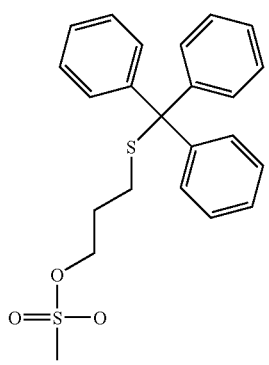

Mesyl chloride (6 µl, 0.075 mmol) was added to a solution of 3-tritylsulfanyl-propan-1-ol (5 mg, 0.015 mmol) and triethyl amine (32 µl, 0.23 mmol) in THF (1 ml). After 30 minutes THF was evaporated under reduced pressure and the crude product dissolved in DCM, washed with a saturated solution of sodium hydrogencarbonate in water, a saturated solution of sodium chloride and dried with is MgSO$_4$. A yield of 10 mg was obtained after evaporation under reduced pressure (analytical HPLC: column Luna C18, 00B-4251-E0: solvents: A=water/0.1% TFA and B=CH$_3$CN/0.1% TFA; gradient 40-80% B over 10 min; flow 1.0 ml /minute; retention time 7.12 minutes detected at 214 and 254 nm). Structure verified by NMR.

1c) Synthesis of (3-fluoro-propylsulfanyl)triphenylmethane

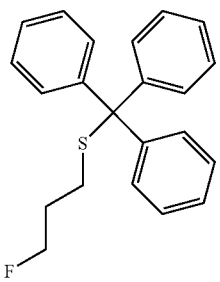

Potassium fluoride (1.4 mg, 0.024 mmol) and Kryptofix 222 (9.0 mg, 0.024 mmol) were dissolved in acetonitrile (0.2 ml) (heating). Methanesulfonic acid 3-tritylsulfanyl-propyl ester (5 mg, 0.012 mmol) in acetonitrile (0.2 ml) was added.

The reaction mixture was heated to 80 degrees for 90 minutes. The crude product was purified by reverse phase preparative chromatography (Vydac 218TP1022 column; solvents A=water/0.1% TFA and B=CH$_3$CN/0.1% TFA; gradient40-90% B over 40 min; flow 10 ml/minute; detection at 254 nm). A yield of 2 mg of purified material was obtained (analytical HPLC: column Phenomenex Luna C18, 00B-4251-E0: solvents: A=water/0.1% TFA and B=CH$_3$CN/0.1% TFA; gradient 40-80% B over 10 min; flow 1.0 ml/minute; retention time 8.2 minutes detected at 214 and 254 nm). Structure verified by NMR.

1d) Synthesis of Fmoc-Lys(Boc)-Cys(StBu)-Arg(Pmc)-Gly-Asp(OtBu)-Cys(StBu)-Phe-Cys(Trt)-Rink Amide AM Resin The title peptide sequence was synthesised on a ABI 433A automatic peptide synthesiser starting with Rink Amide AM resin on a 0.1 mmol scale using 1 mmol amino acid cartridges. The amino acids were pre-activated using HBTU before coupling.

1e) Synthesis of Fmoc-Lys(Boc)-cyclo[Cys($CH_2$)-Arg(Pmc)-Gly-Asp(OtBu)-Cys]-Phe-Cys(Trt)-Rink Amide AM resin.

0.05 mmol of the peptidyl resin prepared as described in 1d) was treated with a solution of 346 μL tributylphosphine, 100 μL water and 2 mL dimethylformamide. The reagents were removed after 90 minutes and the resin washed with dimethylformamide and dichloromethane. The resin was then treated with a solution of 63 mg tetrabutylammoniumfluoride and 2 mL dichloromethane. The reagents were removed by filtration after 2 hours and the resin washed several times with dichloromethane.

The 9-fluorenylmethoxycarbonyl group was removed from the peptidyl resin of 1e) and N-terminal chloroacetylated using chloroacetic acid anhydride. The simultaneous removal of peptide and side-chain protecting groups from the resin was then carried out in 5 mL of trifluoroacetic acid (TFA) containing 2.5% tri-isopropylsilane and 2.5% water for one hour and forty minutes.

Afterwork-up 27 mg of crude peptide was obtained (Analytical HPLC: Gradient, 0-40% B over 10 min where A=$H_2O$/0.1% TFA and B=$CH_3CN$/0.1% TFA; 1 mL/min; column, Phenomenex Luna 3μ C18 (2) 50×4.6 mm; detection, UV 214 nm; product retention time, 7.79 min). Further product charactensation was carried out using electrospray mass spectrometry: Expected, M+H at 1018.3, found, at 1018.3).

1f) Synthesis of Cl—$CH_2$CO-Lys-cyclo[Cys($CH_2$)-Arg-Gly-Asp-Cys]-Phe-Cys-$NH_2$

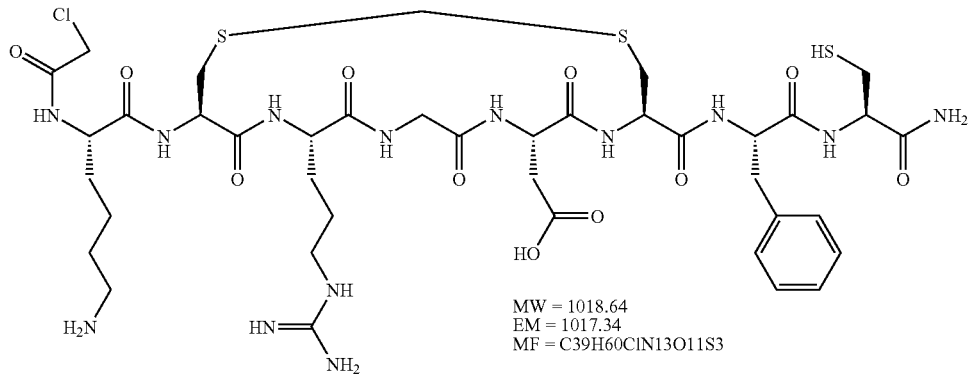

MW = 1018.64
EM = 1017.34
MF = C39H60ClN13O11S3

1g) Synthesis of cyclo[$CH_2$CO-Lys-cyclo[Cys($CH_2$)-Arg-Gly-Asp-Cys]-Phe-Cys-$NH_2$

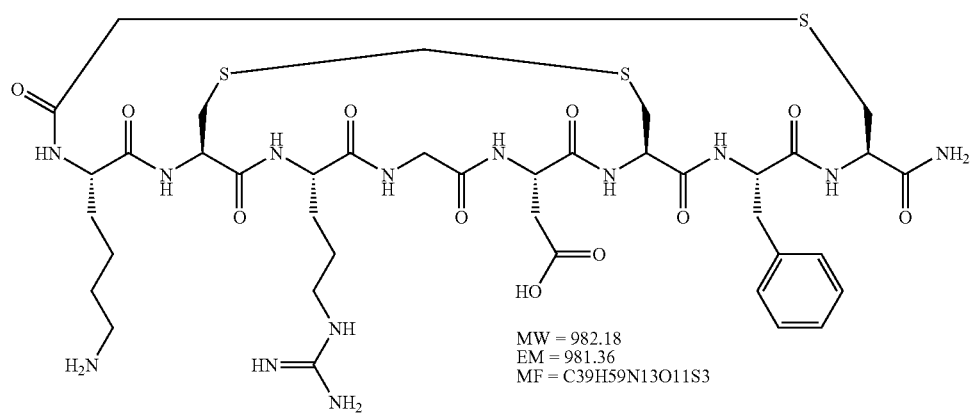

MW = 982.18
EM = 981.36
MF = C39H59N13O11S3

27 mg of peptide product prepared as described in 1f) was dissolved in water/acetonitrile. The mixture was adjusted to pH 8 with ammonia solution and stirred for 2 hours. After lyophilisation 26 mg of the desired product was obtained.

Purification by preparative HPLC (Phenomenex Luna 5μ C18 (2) 250×21.20 mm column) of the crude material was carried out using 0-30% B, where A=H$_2$O/0.1% TFA and B=CH$_3$CN/0.1% TFA, over 40 min at a flow rate of 10 mL/min. After lyophilisation 9 mg of pure material was obtained. (Analytical HPLC: Gradient, 0-30% B over 10 min where A=H$_2$O/0.1% TFA and B=CH$_3$CN/0.1% TFA; flow, 1 mL/min; column, Phenomenex Luna 3μ C18 (2) 50×4.6 mm; detection, UV 214 nm; product retention time, 7.00 min). Further product characterisation was carried out using electrospray mass spectrometry: Expected, M+H at 982.4, found, at 982.3).

1h) Synthesis of cyclo[—CH$_2$CO-Lys(Cl—CH$_2$CO-amino-PEG)-cyclo[Cys(CH$_2$)-Arg-Gly-Asp-Cys]-Phe-Cys-NH$_2$ dissolved in 1 mL dimethylformamide and the mixture stirred for 30 minutes. The reaction was quenched by adding a solution of 25 μL N-methylmorpholine and 2 mL water (pH~9). The mixture was stirred for 2 hours, then evaporated to dryness. The residue was treated with a solution of 5 mL TFA containing 2.5% tri-isopropylsilane and 2.5% water for one hour. TFA was evaporated in vacuo, diethyl ether added to the residue and the resulting precipitate washed with diethyl ether and air-dried. The precipitate was dissolved in 3 mL dimethylformamide together with 8 mg chloroacetic acid anhydride and 9 μL N-methylmorpholine and the mixture stirred for a further 60 minutes. The reaction mixture was evaporated to dryness.

Purification by preparative HPLC (Phenomenex Luna 5μ C18 (2) 250×21.20 mm column) of the crude material was carried out using 5-50% B, where A=H$_2$O/0.1% TFA and B=CH$_3$CN/0.1% TFA, over 40 min at a flow rate of 10 mL/min. After lyophilisation 5 mg of pure material was obtained. (Analytical HPLC: Gradient, 5-50% B over 10 minutes where A=H$_2$O/0.1% TFA and B=CH$_3$CN/0.1% TFA; flow, 1 mL/min; column, Phenomenex Luna 3μ C18 (2) 50×4.6 mm; detection, UV 214 nm; product retention time, 7.08 min). Further product characterisation was carried out

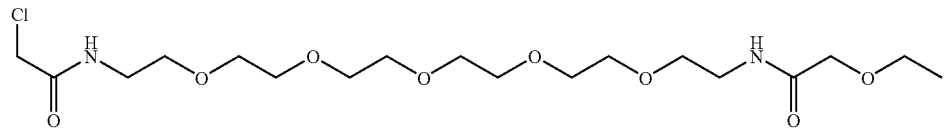

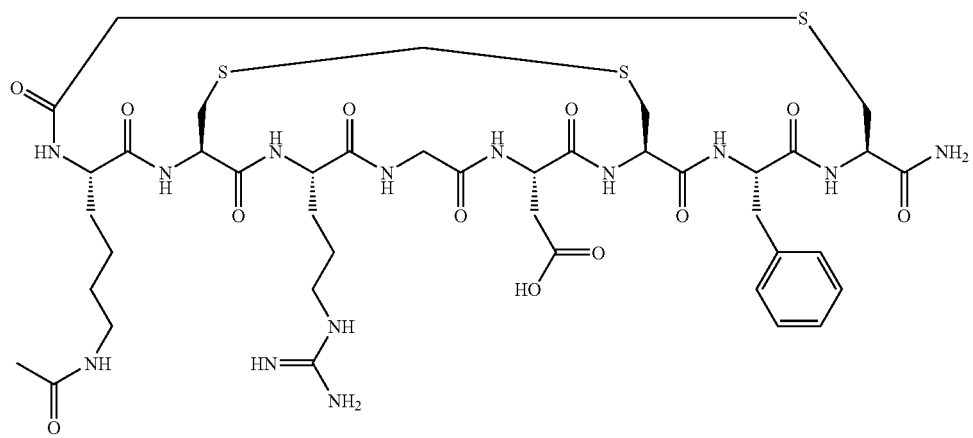

MW = 1437.09
EM = 1435.53
MF = C57H90ClN15O20S3

9 mg of peptide prepared as described in 1g), 34 mg Boc-amino-PEG anhydride and 7 μL N-methylmorpholine were using electrospray mass spectrometry: Expected, M+H at 1436.5, found, at 1436.0).

1i) Site-Specific Conjugation to the Chloroacetyl Modified Peptide

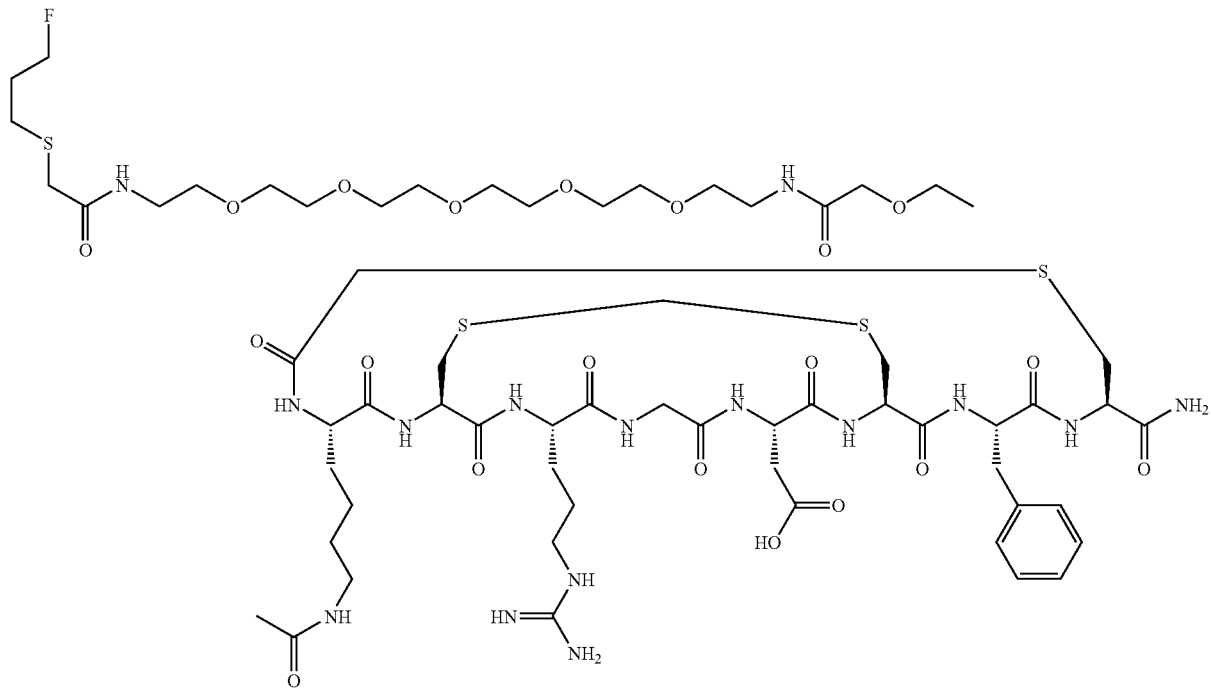

The trityl group from (3-fluoro-propylsulfanyl)triphenyl-methane (2.0 mg, 0.006 mmol) described in 1c) was cleaved with TFA (100 µl) in the presence of TIS (10 µl) and water (10 µl) (5 minutes). The mixture was diluted with 250 µl water and is 250 µl acetonitrile before a solution of c[CH$_2$CO-Lys (ClCH$_2$CO-amino-PEG)-c[Cys(CH$_2$)-Arg-Gly-Asp-Cys]-Phe-Cys]-NH$_2$ (4.0 mg, 0.003 mmol) from 1h) in 500 µl water and 500 µl acetonitrile was added and the pH adjusted to 10 with potassium carbonate buffer (ca 400 µl). The reaction mixture was heated to 60° C. for 50 minutes. The reaction mixture was quenched with TFA and purified using reverse phase preparative chromatography (Phenomenex, C18, 00G-4253-N0 column; solvents A=water/0.1% TFA and B=CH$_3$CN/0.1% TFA; gradient 10-50% B over 30 min; flow 5 ml/minute; detection at 254 nm). A yield of 1.1 mg of purified material was obtained (analytical HPLC: column Vydac 218TP54: solvents: A=water/0.1% TFA and B=CH$_3$CN/0.1% TFA; gradient 10-50% B over 10 min; flow 1.0 ml/minute; retention time 13.20 minutes detected at 214 and 254 nm). Further characterisation was carried out using mass spectrometry, giving m/z value 1494.1.[M–H$^+$] as expected for the desired product.

Example 2

Preparation of a 3-[$^{18}$F]-fluoro-propylsulfanyl Labelled RGD Containing Peptide Title Compound:

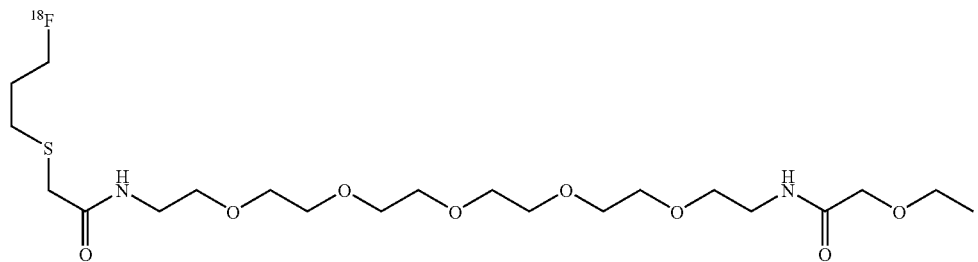

-continued

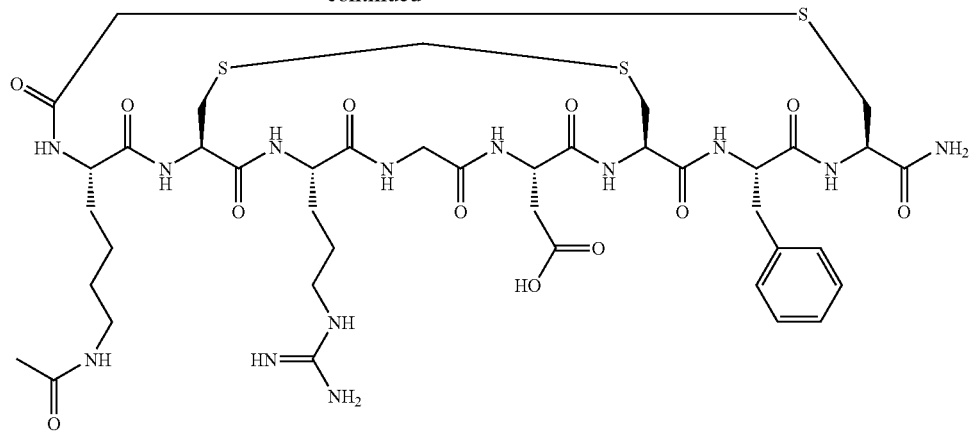

2a) Preparation of ¹⁸F Synthon: (3-[¹⁸F]fluoro-propylsulfanyl)triphenylmethane

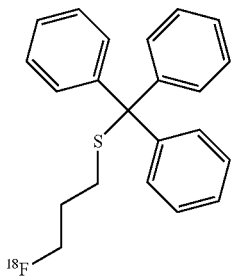

To a Wheaton vial (2 ml) charged with Kryptofix® 222 (10 mg), potassium carbonate (1 mg dissolved in 50 μl water), and acetonitrile (0.8 ml) the fluorine-18 containing water (10 mCi, 1 ml) was added. The solvent was removed by heating at 110° C. for one hour under a stream of nitrogen. Anhydrous acetonitrile (0.5 ml) was added and again evaporated as before. This step was repeated twice. The vial was cooled to room temperature followed by injecting a solution of mesylate prepared as described in Example 2b) (1 mg) in anhydrous DMSO (0.2 ml). The reaction mixture was stirred at 80° C. for 5 min and analysed by HPLC (gradient 1, radiochemical yield 90%).

The reaction mixture was diluted with DMSO/water (1:1 v/v, 0.15 ml) and loaded onto a SepPak-Plus cartridge (ᵗC18, Waters) that had been conditioned (10 ml acetonitrile, 20 ml water). The cartridge was washed with water (10 ml) and the product eluted using acetonitrile. The radiochemical purity was 99%.

2b) Site-Specific Conjugation to the Chloroacetyl Modified Peptide

Deprotection of (3-[¹⁸F]fluoro-propylsulfanyl)triphenylmethane, prepared as described in 2a) and subsequent reaction with the chloroacetyl modified peptide, prepared as described in 1h) is effected using methods analogous to those described in Example 1i).

Biological Data

Using cell membrane preparations known to express the αvβ3 integrin receptor, competitive binding studies were carried out using ¹²⁵I-echistatin and the F-labelled peptides as competing ligand. Binding curves were obtained and $K_i$'s calculated using Prism™ software.

The compound of Example 1, had a $K_i$ of 7 nmole.

What is claimed is:

1. A compound of formula (I):

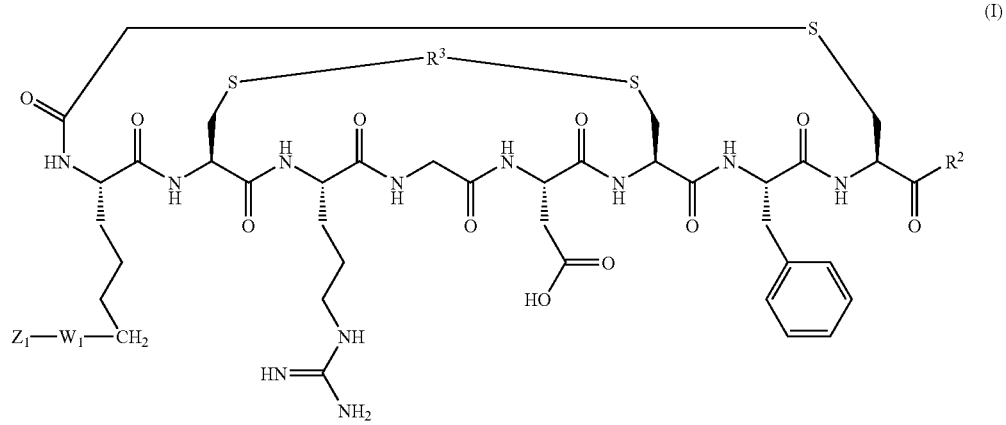

wherein
R² is

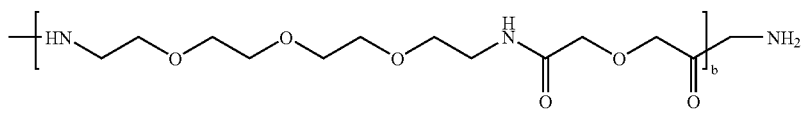

wherein b is an integer of from 0 to 10;

R³ is a $C_{1-4}$ alkylene or $C_{2-4}$ alkenylene bridge;

$W_1$ is absent or represents a spacer moiety which is a $C_{1-30}$ hydrocarbyl group optionally including 1 to 10 heteroatoms selected from oxygen, nitrogen, and sulphur, and is preferentially derived from glutaric and/or succinic acid and/or a polyethyleneglycol based unit and/or a unit of Formula:

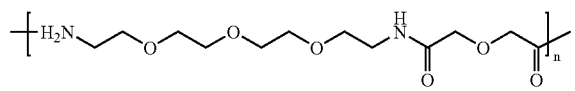

$Z_1$ is an antineoplastic agent, a chelating agent or a reporter moiety.

2. A compound of formula (I) according to claim 1, wherein $Z_1$ is a reporter moiety comprising a radionuclide.

3. A compound of formula (Ia):

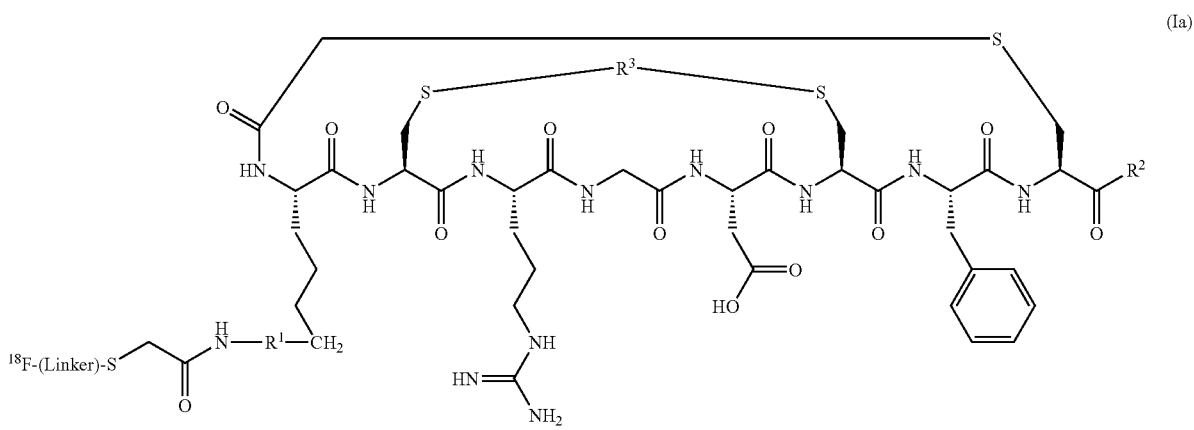

wherein
R¹ is either a bond or is

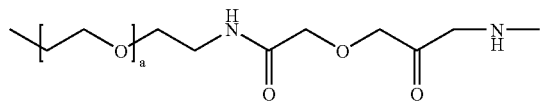

wherein a is an integer of from 1 to 30;
R² is

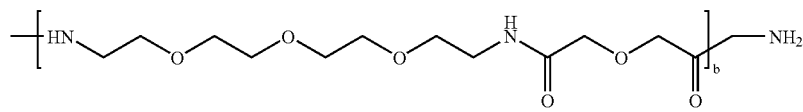

wherein b is an integer of from 0 to 10;

R³ is a $C_{1-4}$ alkylene or $C_{2-4}$ alkenylene bridge;

the Linker is a $C_{1-30}$ hydrocarbyl group optionally including 1 to 10 heteroatoms.

4. A compound of formula (Ia) according to claim 3 in which:

R³ is $C_{1-4}$ alkylene;
a is an integer of from 1 to 10; and
b is 1.

5. A compound of formula (Ia) according to claim 3 in which:

R³ is —CH₂—; and
a is 5.

6. A compound of formula (Ia) according to claim 3 in which the Linker is selected from (II), (III) and (IV):

 (II)

 (III)

-continued

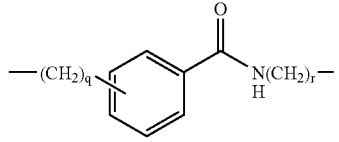 (IV)

wherein:
n is an integer of 1 to 20;
m is an integer of 1 to 10;
p is an integer of 1 to 20;
q is an integer of 0 to 4;
r is an integer of 1 to 10.

7. A compound of formula (Ia) according to claim 3 which is:

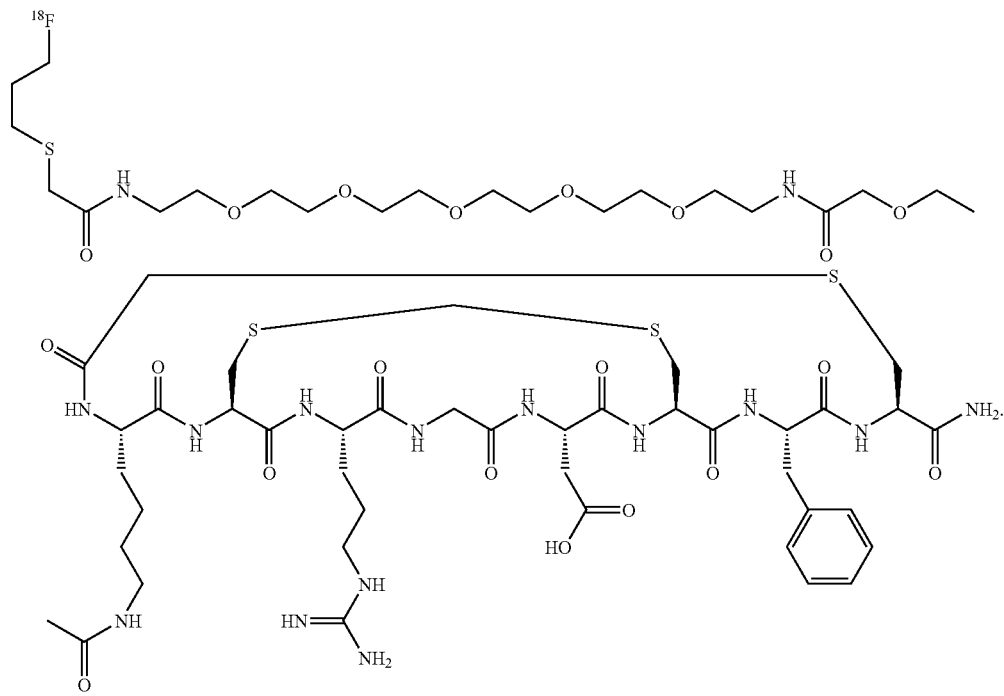

8. A compound of formula (I) according to claim 1 for use in medicine, particularly in the in vivo diagnosis or imaging, for example by PET, of a disease or condition associated with angiogenesis.

9. A radiopharmaceutical formulation comprising a compound of formula (I) according to claim 1 and one or more pharmaceutically acceptable excipients.

10. A method of preparing a compound of formula (Ia) as defined in claim 3 which comprises reaction of the corresponding compound of formula (V):

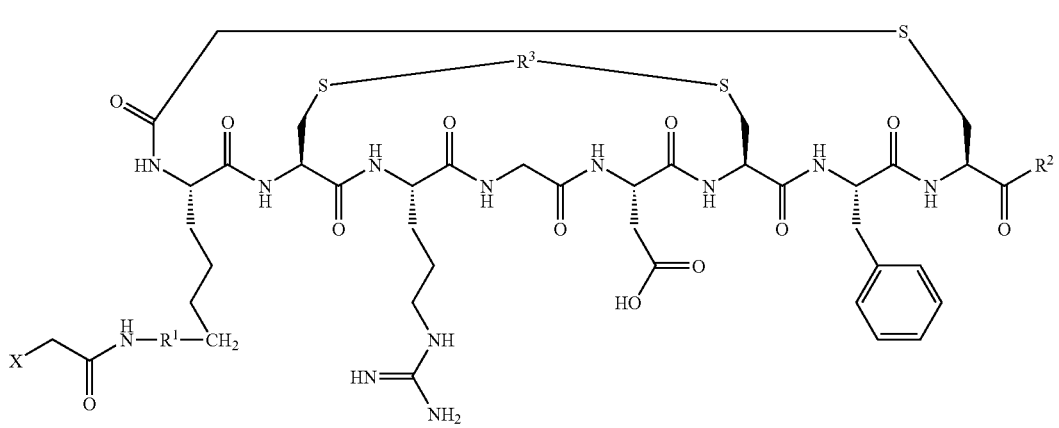

(V)

wherein $R^1$, $R^2$, and $R^3$ are as defined for the compound of formula (Ia) and X is a leaving group selected from chloro, bromo, and iodo, and is preferably chloro;

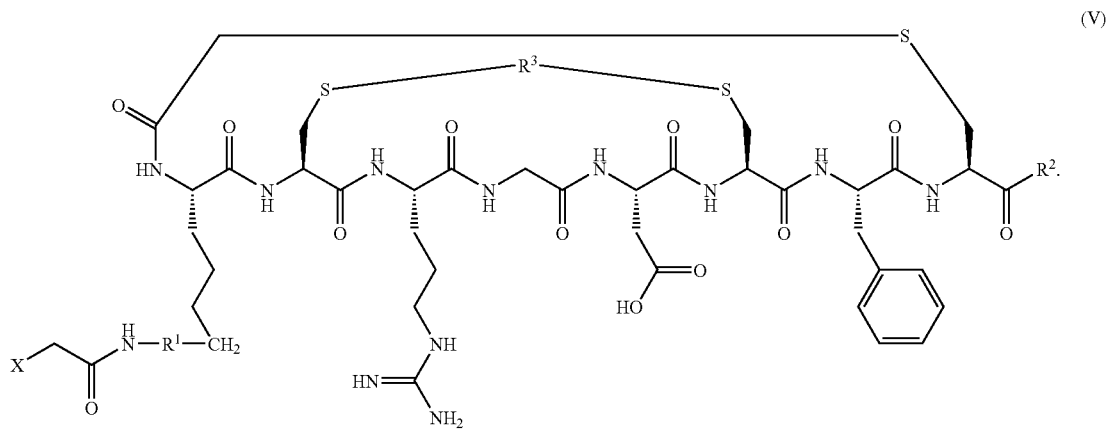

(V)

by reaction with the appropriate compound of formula (VI):

$$^{18}F\text{-(Linker)-SH} \qquad (VI)$$

wherein the Linker is as defined for the compound of formula (Ia).

11. A compound of formula (V) as defined in claim 10.

12. A kit for the preparation of a radiofluorinated peptide of formula (Ia) according to claim 3 comprising:

(i) a compound of formula (VIa)

$$\text{L-(Linker)-SR} \qquad (VIa)$$

wherein L is a leaving group such as p-toluenesulphonate, trifluoromethanesulphonate, or methanesulphonate, the Linker is a $C_{1-30}$ hydrocarbyl group optionally including 1 to 10 heteroatoms;

R is hydrogen or a thiol protecting group; and (ii) an activated peptide of formula (V)

13. A kit according to claim 12, comprising:

(i) a compound of formula (VIb), (VIc), or (VId):

$$\text{L}-(CH_2CH_2O)_n-(CH_2)_m-\text{SR} \qquad (VIb)$$

$$\text{L}-(CH_2)_p-\text{SR} \qquad (VIc)$$

-continued

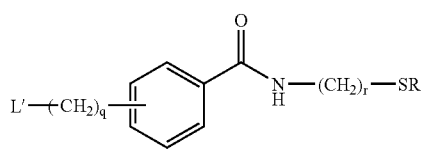

(VId)

n is an integer of 1 to 20;
m is an integer of 1 to 10;
p is an integer of 1 to 20;
q is an integer of 0 to 4;
r is an integer of 1 to 10;
L is a leaving group such as p-toluenesulphonate, trifluoromethanesulphonate, or methanesulphonate;
L' is a leaving group such as iodo, p-toluenesulphonate, trifluoromethanesulphonate, or methanesulphonate and when q is 0, L' can be nitro or an iodonium or ammonium salt, R is hydrogen or a thiol protecting group; and (ii) an activated peptide of formula (V)

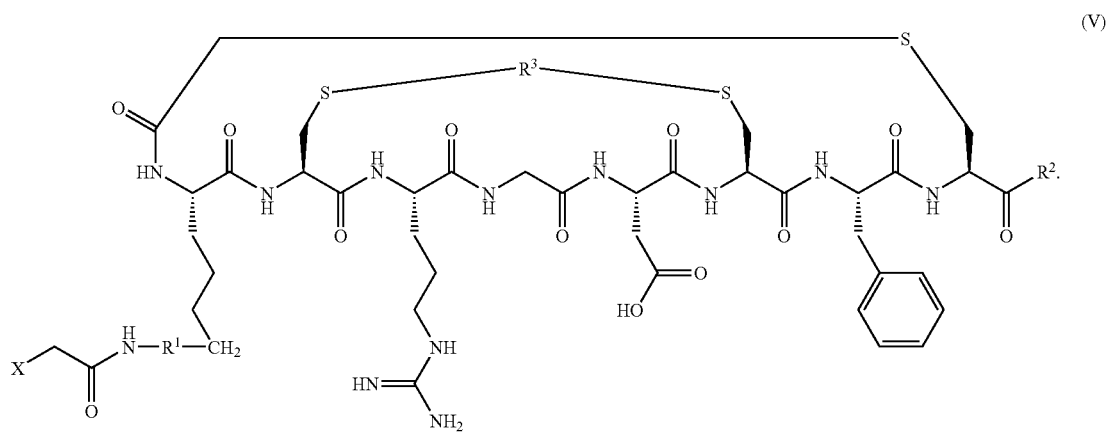

* * * * *